(12) United States Patent
Thomas

(10) Patent No.: US 10,787,427 B2
(45) Date of Patent: Sep. 29, 2020

(54) SYNTHESIS OF FURAN ACIDS FROM XYLONIC ACID

(71) Applicant: Teknologian tutkimuskeskus VTT Oy, Espoo (FI)

(72) Inventor: David Thomas, Espoo (FI)

(73) Assignee: Teknologian tutkimuskeskus VTT Oy, Espoo (FI)

( * ) Notice: Subject to any disclaimer, the term of this patent is extended or adjusted under 35 U.S.C. 154(b) by 0 days.

(21) Appl. No.: 16/643,599

(22) PCT Filed: Sep. 3, 2018

(86) PCT No.: PCT/FI2018/050620
§ 371 (c)(1),
(2) Date: Mar. 2, 2020

(87) PCT Pub. No.: WO2019/043300
PCT Pub. Date: Mar. 7, 2019

(65) Prior Publication Data
US 2020/0207731 A1    Jul. 2, 2020

(30) Foreign Application Priority Data

Sep. 1, 2017 (FI) ..................................... 20175785

(51) Int. Cl.
| | | |
|---|---|---|
| *C07D 307/68* | (2006.01) | |
| *B01J 23/36* | (2006.01) | |
| *B01J 23/38* | (2006.01) | |
| *B01J 27/04* | (2006.01) | |

(52) U.S. Cl.
CPC ............ *C07D 307/68* (2013.01); *B01J 23/36* (2013.01); *B01J 23/38* (2013.01); *B01J 27/04* (2013.01)

(58) Field of Classification Search
CPC ......... C07D 307/68; B01J 23/36; B01J 23/38; B01J 27/04
See application file for complete search history.

(56) References Cited

U.S. PATENT DOCUMENTS

2017/0015643 A1    1/2017  Venkitasubramanian et al.
2018/0086728 A1*   3/2018  Asikainen ............ B01J 37/0203

FOREIGN PATENT DOCUMENTS

| WO | WO 2015189481 A1 | 12/2015 |
| WO | WO 2016166421 A1 | 10/2016 |
| WO | WO2017147098 A1  | 8/2017  |

OTHER PUBLICATIONS

Ahmed et al: Sulfite-Driven. Oxorhenium-Catalyzed Deoxydehydration of Glycols. Organometallics, 2011, vol. 30, pp. 2810-2818.
Li et al: Highly efficient chemical process to convert mucic acid into adipic acid and DFT studies of the mechanism of the rhenium-catalyzed deoxydehydration. Angewandte Chemie International Edition. Mar. 12, 2014. vol. 53, pp. 4200-4204.
Li et al: Highly selective deoxydehydration of tartaric acid over supported and unsupported rhenium catalysts with modified acidities. ChemSusChem, Aug. 25, 2016. vol. 9, pp. 2774-2778.
Shiramizu et al: Expanding the scope of biomass-derived chemicals through tandem reactions based on oxorhenium-catalyzed deoxydehydration. Angewandte Chemie International Edition, Nov. 12, 2013, vol. 52, pp. 12905-12909.
Toivari et al: Low pH D-xylonate production with Pichia kudriavzevii. Bioresource Technology, 2013, vol. 133, pp. 555-562.

* cited by examiner

*Primary Examiner* — Timothy R Rozof
(74) *Attorney, Agent, or Firm* — Laine IP Oy

(57) ABSTRACT

According to an example aspect of the present invention, there is provided a synthesis method for producing furoic acid from a monoacid containing five carbons in the presence of pressure, heat, solvent and catalyst.

13 Claims, 1 Drawing Sheet

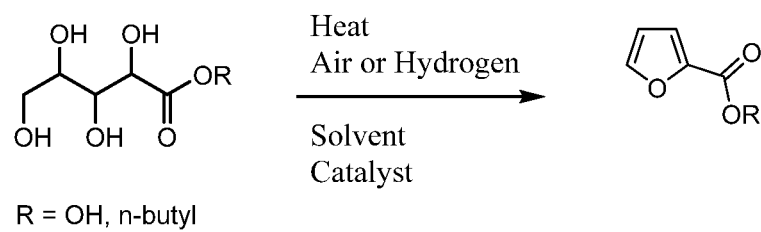

SYNTHESIS OF FURAN ACIDS FROM XYLONIC ACID

FIELD

The present invention relates to synthesis of a furan acid from a monoacid containing five carbon atoms, in particular from xylonic acid.

BACKGROUND

Cellulosic biomass has recently attracted much attention as a renewable feedstock for chemicals and fuels. The industrially relevant compounds are typically produced via crude oil derived processes or by employing biotechnical approaches such as fermentation. However, the price of crude oil is volatile to raw material price fluctuations and crude oil is also negatively recognized by the public as a source of climate change. Another major challenge in the field is that the bio compounds are typically too oxygen-rich to be compatible with the current petroleum-based industry. The search for efficient deoxygenation methods has resulted in a growing interest towards catalytic deoxydehydration (DODH) methods, in order to selectively convert bio-based resources into target chemicals.

One interesting target chemical in this regard is furoic acid, which is an organic compound, typically found in food products as a preservative and a flavoring agent, but also possessing suitable properties in for example nylon preparation and optic technologies. Some methods exist in the prior art for furan production from biomass.

WO 2015/189481 A1 discloses a method for producing furan-2-carboxylic acid. The method uses methyltrioxorhenium catalyst at temperature between 100 and 200° C., reaction time between 15 minutes and 70 hours and hydrogen pressure of 5 bars. Herein the starting raw material is an aldaric acid and thus a C1 moiety is lost reducing the process efficiency and potentially contributing to climate change.

WO 2016/166421 A1 discloses a method for producing furans (FCA or FDCA) and muconic acid from carbon six (C6) diacids by hydrodeoxygenation or dehydration. However, conversion of a C5 monoacid into exclusively FCA is not described nor suggested.

US 2017/015643 A1 discloses a process for converting an aldose sugar to sugar acid and further to a furan molecule. The conversion of an aldonic acid is through a bio-transformation into furoic acid ester via keto-acid intermediate. Use of catalysts is not described.

Ahmad et al. (2011) discloses a method for producing alkenes and furan chemicals by oxorhenium-catalyzed deoxydehydration of polyols. The method is carried out at 150 to 160° C. by using sulphite as a reductant. However, the starting material is not a C5 monoacid.

There is a need for a method of effectively producing furoic acid from sustainable raw materials instead of crude oil sources. Xylose is available from woody biomass but is currently less widely used than other wood components, for example, the lingocellulose. The conversion of xylose into xylonic acid is presented in the publication by Toivari et al. (2013).

SUMMARY OF THE INVENTION

The invention is defined by the features of the independent claims. Some specific embodiments are defined in the dependent claims.

According to an aspect of the present invention, there is provided a method for producing furoic acid from a monoacid containing five carbon atoms (C5) in the presence of specified pressure, heat, catalyst and solvent.

This and other aspects, together with the advantages thereof over known solutions are achieved by the present invention, as hereinafter described and claimed.

The method of the present invention is mainly characterized by what is stated in the characterizing part of claim 1.

Considerable advantages are obtained by means of the invention. For example, the carbon efficiency of the reaction is very good, because all carbons are kept from starting material to target material. Another advantage is that C5 monoacids are exclusively synthesized into furoic acid. Furthermore, a new source of raw material (such as for example xylose) can be utilized as a feedstock for aromatic platform chemicals.

Next, the present technology will be described more closely with reference to certain embodiments.

EMBODIMENTS

The present technology provides means for synthesizing a monoacid, more preferably a monoacid containing five carbon atoms (C5) and in particular xylonic acid exclusively into furoic acid.

FIG. 1 is a diagram showing reaction process scheme of the present invention.

The present invention is based on exposing the monoacid raw material into specified conditions of pressure and heat in the presence of a specified solvent and catalyst in order to exclusively produce the target product, i.e. furoic acid.

One aspect of the present invention is a method for producing furoic acid from a monoacid containing five carbon atoms, by mixing in a pressurized reaction vessel the monoacid or an ester thereof, an alcohol solvent and either a precious metal catalyst or zeolite at temperature between 150 and 250° C. for a pre-determined reaction time to form a solution comprising furoic acid and/or an ester thereof. The solution is then cooled down and the target product is separated and purified by known methods.

According to one embodiment of the present invention, the present method includes the steps of:
 charging the monoacid or an ester thereof to a reaction vessel together with an alcohol solvent and either a precious metal catalyst or a zeolite catalyst to form a reaction mixture,
 pressurising the reaction vessel with hydrogen, air or inert gas to a pressure between 5 to 15 bars,
 heating the reaction mixture to temperature between 150 and 230° C. in said pressurized reaction vessel,
 maintaining the temperature in the pressurized reaction vessel for 0.5 to 36 hours,
 recovering the furoic acid or an ester thereof from the reaction mixture.

In a preferred embodiment of the present invention, the monoacid is xylonic acid or the ester form. Xylonic acid is a particularly potential raw material, since it is renewable and exists in nature in great amounts. It is also known in the art how to convert xylose, which is a non-edible sugar originating for example from trees, into xylonic acid and thus into a suitable raw material for use in the present invention.

In one embodiment of the present invention the reaction temperature inside the reaction vessel is between 150 and 165° C. This is essentially lower temperature than what has been published earlier in the art relating to furan synthesis technology. However, reaction temperatures ranging from 150 to 250° C. are all within the scope of the present invention.

In one embodiment of the present invention, the solvent is selected from, but not limited to, methanol, ethanol, butanol and pentanol. In particularly butanol has shown good suitability for the present method, as becomes evident from the examples of the present invention.

In one embodiment of the present invention, the catalyst is either methyltrioxoyrhenium or sulphonic acid ethyl sulphide silica, which have both proven to work in a desired way.

In one embodiment of the present method, the pressure inside the reaction vessel is adjusted between 5 to 10 bars, most suitably to about 10 bars.

It is to be understood that the embodiments of the invention disclosed are not limited to the particular process steps or materials disclosed herein, but are extended to equivalents thereof as would be recognized by those ordinarily skilled in the relevant arts. It should also be understood that terminology employed herein is used for the purpose of describing particular embodiments only and is not intended to be limiting.

Reference throughout this specification to one embodiment or an embodiment means that a particular feature, structure, or characteristic described in connection with the embodiment is included in at least one embodiment of the present invention. Thus, appearances of the phrases "in one embodiment" or "in an embodiment" in various places throughout this specification are not necessarily all referring to the same embodiment. Where reference is made to a numerical value using a term such as, for example, about or substantially, the exact numerical value is also disclosed.

As used herein, a plurality of items, structural elements, compositional elements, and/or materials may be presented in a common list for convenience. However, these lists should be construed as though each member of the list is individually identified as a separate and unique member. While the forgoing examples are illustrative of the principles of the present invention in one or more particular applications, it will be apparent to those of ordinary skill in the art that numerous modifications in form, usage and details of implementation can be made without the exercise of inventive faculty, and without departing from the principles and concepts of the invention. Accordingly, it is not intended that the invention be limited, except as by the claims set forth below.

The verbs "to comprise" and "to include" are used in this document as open limitations that neither exclude nor require the existence of also un-recited features. The features recited in depending claims are mutually freely combinable unless otherwise explicitly stated. Furthermore, it is to be understood that the use of "a" or "an", that is, a singular form, throughout this document does not exclude a plurality.

INDUSTRIAL APPLICABILITY

Furoic acid finds industrial application for example as a preservative in food products, acting as a bactericide and fungicide. It is also considered as an acceptable flavoring ingredient and achieved a generally recognized as safe (GRAS) status. Furoic acid may also have an important role in optic technology; on-going studies have shown that furoic acid crystals have several favorable properties of nonlinear optical materials.

EXAMPLES

General Method

Product yields were determined using GC-FID with external calibration for each product compound. Standard esterification methods of the corresponding carboxylic acids were used to produce the ester standards for the calibrations. The analyses were done with Shimadzu GC-1020 Plus Gas Chromatograph. The column used was ZB-5HT Inferno and the temperature program 100° C./1 min→10° C./min to 280° C./hold time 1 min→30° C./min to 350° C./hold time 5 min. Injector temperature 320° C., detector temperature 380° C., carrier gas helium, pressure 100.2 kPa, total flow 103.8 ml/min, column flow 1.00 ml/min, linear velocity 27.5 cm/sec, purge flow 3.0 ml/min, injection volume 1.0 µl, split ratio 100. All reaction fractions were silylated with standard methods prior to GC-FID analysis. Yields are interpreted from GC-FID. The results were confirmed using GC-MS.

Set 1: Methyl Trioxo Rhenium

Xyonic acid butyl ester (1.0 g, 4.50 mmol), methyl trioxo rhenium (0.45 mmol, 10 mol %) and butanol (10 ml) were charged in the reaction vessel. The reaction vessel was pressurized with hydrogen (10 bar) and heated up to the reaction temperature (Table 1). After the indicated reaction time the mixture was cooled down to room temperature, any solid precipitate was filtered, washed with butanol (5 ml) and dried. The solvent fraction was concentrated in a rotary evaporator to afford product. The product was isolated to afford 2-furoic acid n-butyl ester: $^1$H NMR (500 MHz, CDCl$_3$): δ 0.90 (m, 3H, CH$_3$), 1.41 (m, 2H, CH$_2$), 1.75 (m, 2H, CH$_2$), 4.3 (m, 2H, CH$_2$), 6.51 (m, 1H, Ar—H), 7.17 (m, 1H, Ar—H), 7.58 (m, 1H, Ar—H), mz 168, 112, 95.

TABLE 1

| | Reaction Conditions | | | |
|---|---|---|---|---|
| Entry | Catalyst loading/wt % | T/° C. | t/h | Furoic acid ester Yield/% |
| 1 | 10 | 160 | 36 | 11 |
| 2 | 30 | 230 | 36 | 62 |
| 3 | 10 | 230 | 36 | 1 |

Set 2: Phenyl Sulfonic Acid Ethyl Sulfide Silica

To a pressure reactor equipped with magnetic stirring bar were charged the n-butanol (20 ml), xylonic acid butyl ester (1.0 g) and phenyl sulfonic acid ethyl sulfide silica (100 mg). The reactor was closed, pressurized with air to 6 bar and heated to the reaction temperature for indicated time. The reaction could be performed under air or inert gases. After the indicated reaction time, the solid and liquid phases were separated, and organic compounds from the solid phase were extracted with hot solvent. Evaporation afforded brown oil, 2-furoic acid n-butyl ester: $^1$H NMR (500 MHz, CDCl$_3$): δ 0.90 (m, 3H, CH$_3$), 1.41 (m, 2H, CH$_2$), 1.75 (m, 2H, CH$_2$), 4.3 (m, 2H, CH$_2$), 6.51 (m, 1H, Ar—H), 7.17 (m, 1H, Ar—H), 7.58 (m, 1H, Ar—H), mz 168, 112, 95. (Table 2)

TABLE 2

| | Reaction Conditions | | | | |
|---|---|---|---|---|---|
| Entry | Catalyst loading/wt % | T/° C. | t/h | Additive/ wt % | Furoic acid butyl ester Yield/% |
| 1 | 10 | 150 | 21 | — | 19 |
| 2 | 10 | 230 | 24 | — | 42 |
| 3 | 10 | 230 | 2 | — | 29 |
| 4 | 50 | 150 | 24 | — | 9 |
| 5 | 10 | 150 | 24 | H$_2$SO$_4$ | 1 |

CITATION LIST

Patent Literature

1. WO 2015/189481 A1
2. WO 2016/166421 A1
3. US 2017/015643 A1

Non-Patent Literature

1. Ahmad, I., Chapman, G., Nicholas, K. M., *Sulfite-Driven. Oxorhenium-Catalyzed Deoxydehydration of Glycols*, Organometallics, 2011, Vol 30, pp. 2810-2818.
2. Toivari, M., Vehkomäki, M.-L., Nygård, Y., Penttilä, M., Ruohonen, L., Wiebe, M. G., *Low pH D-xylonate production with Pichia kudriavzevii*, Bioresource Technology, 2013, Vol. 133, pp. 555-562.

The invention claimed is:

1. A method for producing furoic acid and/or an ester thereof comprising mixing in a pressurized reaction vessel a monoacid comprising five carbon atoms or an ester thereof, an alcohol solvent and a catalyst comprising a precious metal catalyst or a zeolite catalyst at a reaction temperature between 150 and 250° C. for a pre-determined reaction time to form a solution comprising the furoic acid and/or the ester thereof.

2. The method according to claim 1, wherein the reaction time is between 2 to 36 hours.

3. The method according to claim 1, wherein the method comprises:
   charging the monoacid and/or ester thereof to the pressurized reaction vessel together with the alcohol solvent and the catalyst to form a reaction mixture,
   pressurising the reaction vessel with hydrogen, air or inert gas to a pressure between 5 to 15 bars,
   heating the reaction mixture to temperature between 150 and 230° C. in said pressurized reaction vessel,
   maintaining the temperature in the pressurized reaction vessel for 0.5 to 36 hours,
   recovering the furoic acid and/or ester thereof from the reaction mixture.

4. The method according to claim 1, wherein the monoacid is xylonic acid.

5. The method according to claim 1, wherein the reaction temperature is between 150 to 165° C.

6. The method according to claim 1, wherein the solvent is selected from the group consisting of methanol, ethanol, butanol, and pentanol.

7. The method according to claim 1, wherein the catalyst comprises methyltrioxorhenium or sulphonic acid ethyl sulphide silica.

8. The method according to claim 1, wherein the pressure inside the reaction vessel is adjusted between 5 to 10 bars.

9. The method according to claim 1, wherein the solvent comprises butanol.

10. The method according to claim 1, wherein the pressurized reaction vessel comprises a pressure of from 5 to 10 bars.

11. The method according to claim 1, wherein the process comprising mixing the ester of the monoacid in the pressurized reaction vessel with the alcohol solvent and the catalyst, and wherein the ester thereof comprises xylonic acid butyl ester.

12. The method according to claim 1, wherein the catalyst comprises a precious metal catalyst.

13. The method according to claim 1, wherein the catalyst comprises a zeolite catalyst.

* * * * *